(12) United States Patent
Demirel et al.

(10) Patent No.: US 8,647,654 B2
(45) Date of Patent: Feb. 11, 2014

(54) METHOD AND SYSTEMS FOR FORMING AND USING NANOENGINEERED SCULPTURED THIN FILMS

(75) Inventors: Melik C. Demirel, State College, PA (US); Akhlesh Lakhtakia, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 1195 days.

(21) Appl. No.: 11/639,850

(22) Filed: Dec. 15, 2006

(65) Prior Publication Data

US 2007/0148206 A1    Jun. 28, 2007

Related U.S. Application Data

(60) Provisional application No. 60/753,025, filed on Dec. 22, 2005.

(51) Int. Cl.
*A61F 2/00* (2006.01)
*B05D 3/00* (2006.01)

(52) U.S. Cl.
USPC .......................................... 424/423; 424/2.24

(58) Field of Classification Search
None
See application file for complete search history.

(56) References Cited

U.S. PATENT DOCUMENTS

| | | | |
|---|---|---|---|
| 3,011,920 A | 12/1961 | Shipley | |
| 4,005,238 A | 1/1977 | Gaehde et al. | |
| 4,123,308 A | 10/1978 | Nowlin et al. | |
| 4,960,050 A | 10/1990 | Hatch | |
| 5,104,480 A | 4/1992 | Wojnarowski et al. | |
| 5,824,049 A * | 10/1998 | Ragheb et al. | 623/1.44 |
| 5,866,204 A * | 2/1999 | Robbie et al. | 427/256 |
| 5,866,430 A | 2/1999 | Grow | |
| 6,248,422 B1 | 6/2001 | Robbie et al. | |
| 6,270,846 B1 | 8/2001 | Brinker et al. | |
| 6,436,615 B1 | 8/2002 | Brandow et al. | |
| 7,004,976 B2 | 2/2006 | Ornberg et al. | |
| 7,057,881 B2 | 6/2006 | Chow et al. | |
| 7,462,750 B2 | 12/2008 | Hanefeld et al. | |
| 2002/0026086 A1 | 2/2002 | Dolbier, Jr. et al. | |
| 2004/0146560 A1 | 7/2004 | Whiteford et al. | |
| 2005/0181195 A1 | 8/2005 | Dubrow | |
| 2005/0227055 A1 | 10/2005 | Senkevich et al. | |
| 2006/0207878 A1 * | 9/2006 | Myung et al. | 204/403.09 |
| 2006/0252065 A1 | 11/2006 | Zhao et al. | |
| 2006/0257968 A1 | 11/2006 | Van Duyne et al. | |
| 2007/0004046 A1 | 1/2007 | Abbott | |
| 2007/0042609 A1 | 2/2007 | Senkevich et al. | |
| 2007/0099019 A1 | 5/2007 | Hanefeld et al. | |
| 2007/0148206 A1 | 6/2007 | Demirel et al. | |
| 2007/0166539 A1 | 7/2007 | Zhao et al. | |
| 2008/0144026 A1 | 6/2008 | Zhao et al. | |
| 2008/0268226 A1 | 10/2008 | Demirel et al. | |
| 2008/0269456 A1 | 10/2008 | Lahann et al. | |
| 2009/0257056 A1 | 10/2009 | Demirel et al. | |
| 2009/0269587 A1 | 10/2009 | Dressick et al. | |

FOREIGN PATENT DOCUMENTS

| | | |
|---|---|---|
| WO | WO 98/03695 | 1/1998 |
| WO | WO 2005/108460 A1 | 11/2005 |

OTHER PUBLICATIONS

Karuri et al. in Journal of Cell Science 117, 3153-3164, 2004.*
Teixeira et al. in Journal of Cell Science 116, 1881-1892, 2003.*
Evans et al. in Journal of Biomedical and Materials Research 46, 485-493, 1999.*
Pursell et al. in Polymer 46 (2005) 9544-9548.*
Lakhtakia, A., et al. "Sculptured Thin Films (STFS) for Optical, Chemical and Biological Applications" Innovations in Materials Research, vol. 1, No. 2 (1996) pp. 165-176.
Montgomery, D. J., et al. "Optically Active Fluorite Films" Nature, vol. 183, Jan. 10, 1959, pp. 104-105.
Motohiro, Tomoyoshi et al. "Thin Film Retardation Plate by Oblique Deposition" Applied Optics, vol. 28, No. 13, Jul. 1, 1989, pp. 2466-2482.
Nieuwenhuizen, J. M. et al. "MIcrofractography of Thin Films" Philips Research Laboratories, 1966, No. 3/4, pp. 87-91.
Pursel, Sean et al. "Growth of Sculptured Polymer Submicronwire Assemblies by Vapor Deposition" www.elsevier.com/locate/polymer, Polymer, 2005; pp. 9544-9548.
International Search Report in PCT/US2009/041868, dated Aug. 18, 2009 (1 page).
International Search Report in PCT/US2009/046084, dated Aug. 7, 2009 (2 pages).

* cited by examiner

*Primary Examiner* — Dennis Heyer
(74) *Attorney, Agent, or Firm* — Brinks Gilson & Lione; Ryan L. Marshall (57) ABSTRACT

A method of forming a sculptured thin film on a surface includes rotating the surface and depositing a sculptured thin film comprised of a polymer on the surface to form submicron or nanoscale wires during the step of rotating. The submicron wires may be columnar, helically columnar, chevron shaped, chiral shaped, distinct or interwoven. The depositing step may involve pyrolizing the polymer into a vapor of monomers, directing the vapor of monomers towards the surface while rotating the surface, and polymerizing the monomers on the surface. The surface may be incorporated into biomedical device or other biological application where the sculptured thin film is biocompatible and bioactive and adapted for a biological use.

34 Claims, 6 Drawing Sheets
(5 of 6 Drawing Sheet(s) Filed in Color)

METHOD AND SYSTEMS FOR FORMING AND USING NANOENGINEERED SCULPTURED THIN FILMS

CROSS-REFERENCE TO RELATED APPLICATIONS

This application claims priority under 35 U.S.C. §119 to U.S. Provisional Patent Application No. 60/753,025, filed Dec. 22, 2005, herein incorporated by reference in its entirety.

BACKGROUND OF THE INVENTION

The present invention relates to nanoengineered sculptured thin films, and more particularly to nanoengineered sculptured thin films suitable for biological uses. Various references in the prior art have discussed the formation of sculptured thin films. Among these are U.S. Pat. No. 5,866,204 to Robbie et al. and U.S. Pat. No. 6,248,422 also to Robbie et al., which refer to sculptured thin film as sculpted thin film [1,2] and a corresponding publication [3]. To be clear, sculpted thin film refers to deposited films deposited in a manner to simulate a geometric form. Earlier works illustrate that as early as 1959 it was known to provide a substrate which is (i) inclined at a fixed angle about an axis parallel to the substrate plane; and (ii) which rotates about an axis passing normally 20 through the substrate plane during a deposition process. Young and Kowal disclose such a method [4]. Such a method is also disclosed by Dawson and Young [5]. In addition, work such as the 1989 paper by Motohiro and Taga contains SEM images of the resulting change in the geometry of a microstructure, including V-shaped columns [6].

References such as U.S. Pat. No. 5,866,204 to Robbie et al. and U.S. Pat. No. 6,248,422 also to Robbie et al. recognize the possibility of biocompatible sculptured thin film and potential uses [1,2]. In other work, various biocompatible substrates have been grown in micro and nanoscales and they have been used to control cell adhesion [7-10]. It is known that the topography of the surface alters proliferation, [11-13] and differentiation [14-16]. It has been also shown that submicron-scale features activate macrophage cell 30 adhesion and regulate the amount of F-actin in cells [17]. Recent research by Karuri et al. has shown that cell attachment on silicon columnar films can be dependent on nanoscale topography [18]: nanostructured surfaces affect cell morphology of human corneal epithelial cells. However, the long-term degradation of silicon interacting with biofluids is problematic, and the structures made heretofore require complicated and expensive techniques (e.g., lithography and masking). Alternative biological bottom-up technologies employ natural and artificial biopolymers such as collagen as bioactive surfaces. However, elevated medically significant environmental factors (e.g., temperature, pH, contaminants, and sterilizing agents and detergents) degrade biopolymers. Therefore, despite various advances made problems remain.

It should be appreciated that of the many advances in medicine during the last two decades, the engineering of implantable artificial organs and prosthetic devices is very exciting. Implantability requires that the device be biocompatible at least, and achieving bioactivity would be even better. Biological cells have been grown on nanostructured surfaces, which suggest the significance of nanomorphology for all surfaces of an implanted device that are going to be in contact with biological tissue. There is a growing realization that ongoing research in the areas of fundamental surface biology, nanofabrication, and recombinant DNA technologies will provide enhanced 3-dimensional tissues designed to accomplish specific biological and medical goals.

Imagine making a tissue sheet that can act as a filter in a kidney dialysis machine. Imagine a tissue sheet functioning inside a living heart as a tricuspid valve to regulate blood flow between an auricle and ventricle. Imagine a tissue sheet that will promote bone growth around a total knee replacement by ensuring that certain types of cells proliferate in comparison with others. What is needed is a biocompatible and bioactive material and methods of using the material in medical or other biological applications. As used herein, the term "bioactive" generally refers to components that bind to tissue. The term "biocompatible" refers to materials which are acceptable for at least some biological applications, and in particular may be compatible with tissue.

BRIEF SUMMARY OF THE INVENTION

Therefore, it is a primary object, feature, or advantage of the present invention to improve upon the state of the art.

It is a further object, feature, or advantage of the present invention to provide for a method for forming sculptured thin films.

It is a further object, feature, or advantage of the present invention to provide for the use of biocompatible and bioactive STFs that can made of organic and inorganic materials such as, without limitation, polymers, oxides, and metals.

Another object, feature, or advantage of the present invention to provide biocompatible and bioactive STFs which can be used with human cells, including HEK-293 human kidney cells and COS7 fibroblast cells.

Yet another object, feature, or advantage of the present invention is to provide means to promote cell differentiation, proliferation, and adhesion that can be designed to suit different types of cellular matter.

A further object, feature, or advantage of the present invention is to provide a biocompatible material that can be made through a direct one-step growth procedure without requiring masking and/or lithography.

A still further object, feature, or advantage of the present invention is to provide a biocompatible material which can be deposited on topographic substrates.

Yet another object, feature, or advantage of the present invention to provide a biocompatible material that can be deposited in various forms.

A still further object, feature, or advantage of the present invention is to provide a biocompatible material having a surface upon which topography may be created through masking, lithography, and/or other processes.

Another object, feature, or advantage of the present invention is to provide a biocompatible material that can be applied to biological as well as non-biological surfaces either directly or through an adhesive.

Yet another object, feature, or advantage of the present invention is to provide a biocompatible and bioactive material that can be used for drug delivery as well as drug encapsulation.

A further object, feature, or advantage of the present invention is to provide a biocompatible and bioactive material that can simultaneously deliver nutrients and genes for diagnostic and therapeutic purposes.

Another object, feature, or advantage of the present invention is use of a biocompatible and bioactive material for coating forming mandrels, catheters, guide wires, stents, sensors, transducers, and probes.

Yet another object, feature, or advantage of the present invention is the use of a biocompatible and bioactive material for biological cultures, implanted biosensors and neural interfaces, and for use to prevent fibrous encapsulation and thus increase mutual adherence of different pairs of tissue types.

A further object, feature, or advantage of the present invention is the use of a biocompatible and bioactive material that provides a nanostructured surface with affecting cell morphology.

A still further object, feature, or advantage of the present invention is the use of a biocompatible material that is not associated with long-term degradation which interacts with biofluids.

Another object, feature, or advantage of the present invention is to provide for the use of a biocompatible material which does not require complicated and expensive techniques.

Yet another object, feature, or advantage of the present invention is the use of a biocompatible material which has a controllable porosity.

A still further object, feature, or advantage of the present invention is the use of a biocompatible material which possesses an engineerable shape.

Yet another object, feature, or advantage of the present invention is the use of a biocompatible material for the simultaneous delivery of drugs, nutrients, and/or genes.

A further object, feature, or advantage of the present invention is to provide a bioactive surface which is not biopolymer susceptible to degradation due to elevated medically significant environmental factors such as temperature, pH, contaminants, sterilizing agents, and detergents.

Another object, feature, or advantage of the present invention is the provision of biocompatible materials with well-controlled interfaces between the living system and other systems.

Yet another object, feature, or advantage of the present invention is to provide thin films suitable for use in cell attachment applications and in tissue engineering.

One or more of these and/or other objects, features, or advantages of the present invention will become apparent from the specification and claims that follow. The present invention is not, however, to be limited by or to these stated objects, features, or advantages.

According to one aspect of the present invention, a method of forming a sculptured thin film on a surface includes rotating the surface and depositing a sculptured thin film comprised of a para-xylylene derivative polymer on the surface to form submicron wires during the step of rotating. The submicron wires may be columnar, helically columnar, chevron shaped, chiral shaped, distinct or interwoven. The depositing step may involve pyrolizing the para-xyxlylene derivative polymer into a vapor of monomers, directing the vapor of monomers towards the surface while rotating the surface, and polymerizing the monomers on the surface. The surface may be incorporated into biomedical device or other biological application where the sculptured thin film is biocompatible and bioactive and adapted for a biological use.

According to another aspect of the present invention a method of forming a sculptured thin film on a surface includes rotating the surface, pyrolizing a polymer into a vapor of monomers, directing the vapor of monomers towards the surface while rotating the surface, and forming a plurality of sculptured thin film wires through polymerization of the monomers on the surface, each of the sculptured thin film wires having a diameter of less than 200 nm. The step of rotating the surface controls shape of the sculptured thin film wires. The polymer may be a polymer which is biocompatible and bioactive, such as, but not limited to a para-xylylene derivative polymer.

According to another aspect of the invention, a method of using a sculptured thin film includes applying a sculptured thin film to a surface, the sculptured thin film being biocompatible and bioactive and adapted for a biological use, and using the sculptured thin film for the biological use. The biological use may include differentiation, proliferation and adhesion of eukaryotic and prokaryotic cellular matter. The sculptured thin film may include organic material, including organic material resulting from treatment of an organic material. The sculptured thin film may be of inorganic material such as a polymer.

According to another aspect of the present invention a system includes a living system and a substrate comprising a sculptured thin film adapted for interaction with a living system. The sculptured thin film is biocompatible and bioactive relative to the living system and interacts with the living system. The sculptured thin film may be used to deliver a drug to the living system, delivering a nutrient to the living system, or delivering a gene to the living system.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

I. Formation of Polymeric STFs

The present invention provides for the formation of polymeric sculptured thin films (STFs) through use of a combination of physical and chemical vapor deposition processes. The process allows the shapes of submicron and nanowire assemblies to be engineered so that the resulting polymeric STF acts as a template for preferential attachment of biomolecules.

Figure 1:
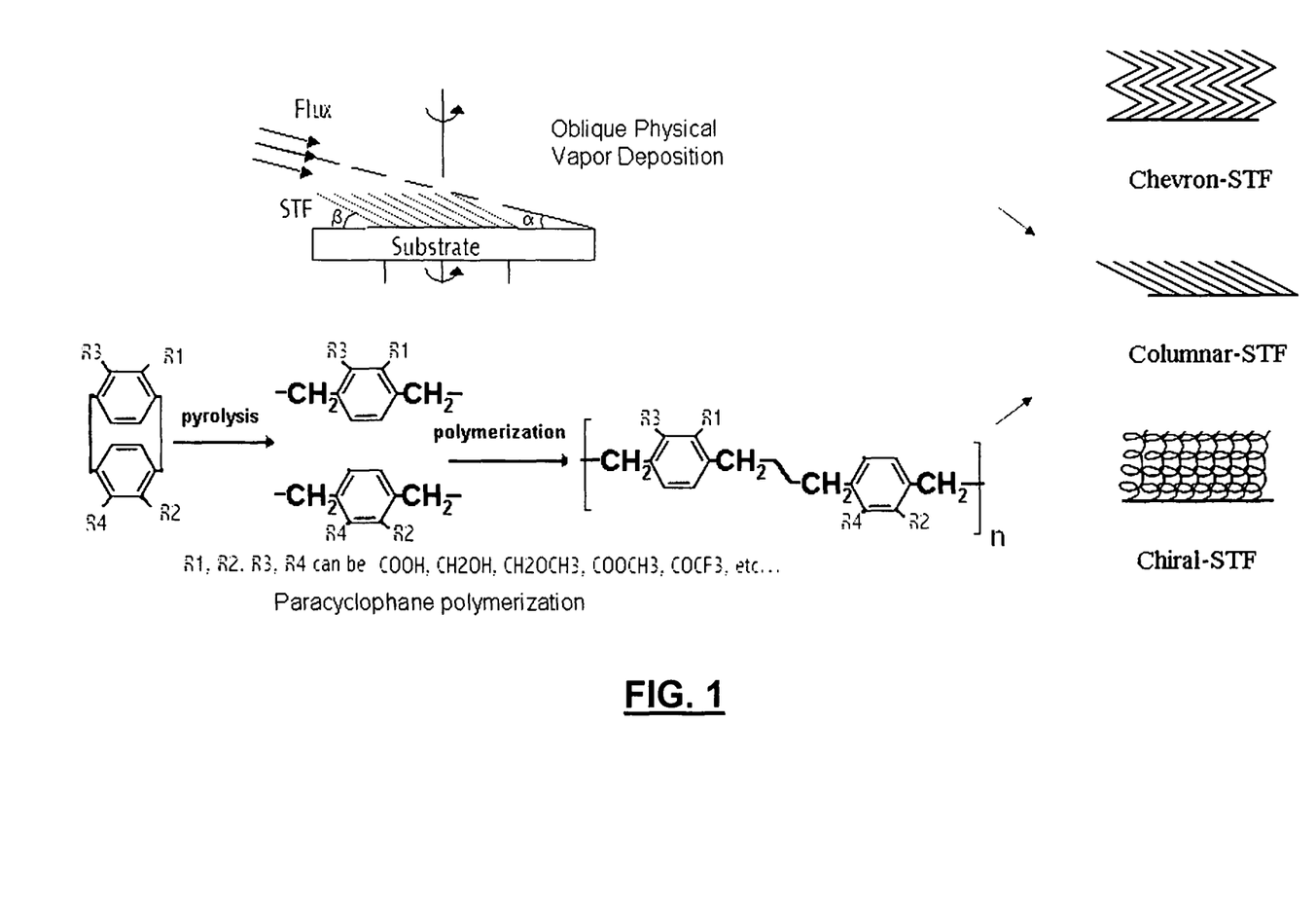
FIG. 1 provides a pictorial representation of one embodiment of a methodology for forming STFs.

FIG. 1 is a pictorial representation of a method of forming polymeric STFs. The process of growing the STFs may be grown in a commercial reactor such as the Parylene Deposition System (PDS) 2010 from Cookson Electronics modified through the addition of a nozzle for controlling direction of vapor deposition and through addition of a motorized assembly to control movement of the substrate. The deposition process involves vaporization of the dimer until it sublimes pyrolysis to form the monomer and polymerization of the parylene or other polymer on the substrate. Note that chemical and physical vapor depositions were performed in combination. Dimers of the paracylophane are pyrolized into a vapor of monomers. This vapor or flux is directed obliquely towards a rotating substrate. The vapor flux is controlled by the evaporation temperature of the dimer and the pyrolyzing temperature. The two temperatures together control the deposition rate and deposition pressure. The monomer coalesces on the substrate and then polymerizes to form the STFs. The STF wires formed may take various shapes as can be controlled by the movement of the substrate during the deposition process. The shapes can include, for example, columnar, helically columnar, chevron, and chiral shapes. The STF wires may be separate and distinct or may be interwoven.

Figure 2:
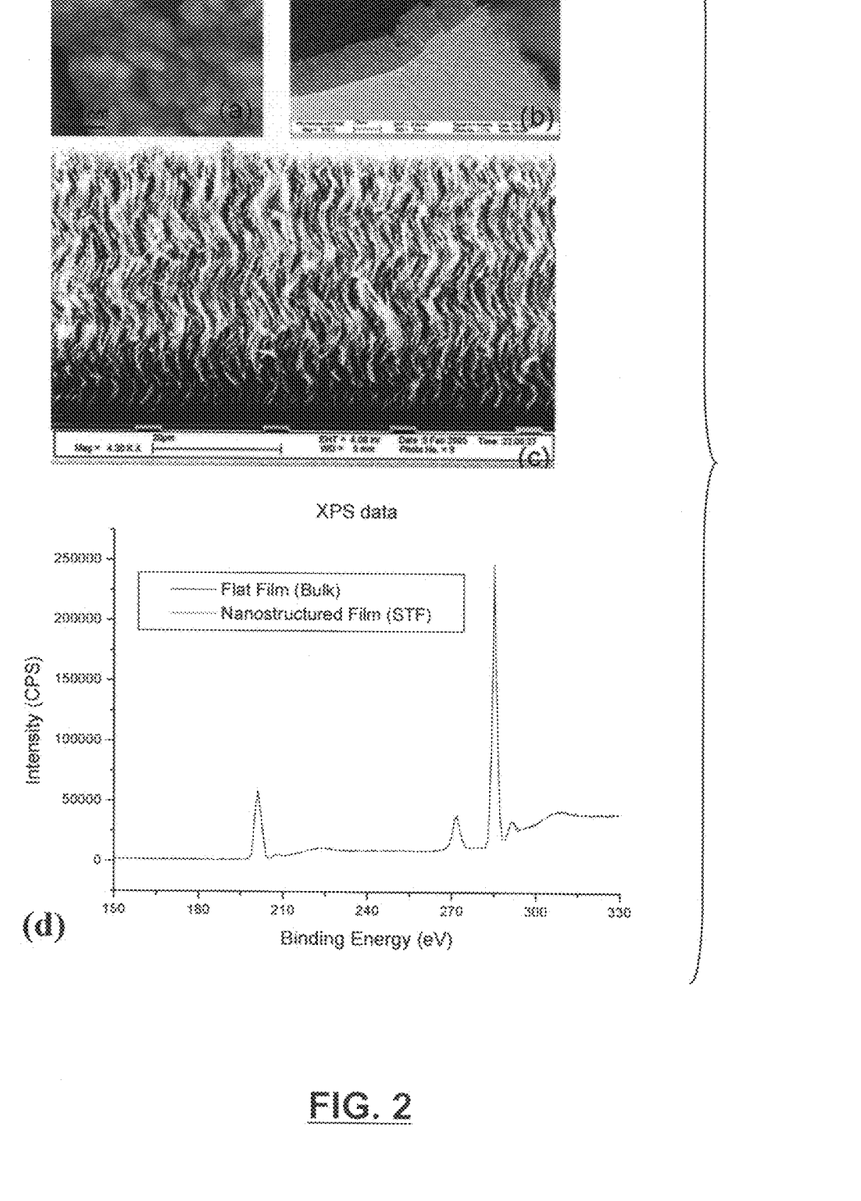
FIG. 2 provides a top surface AFM image of the nanostructured paracyclophane thin film (STF) showing that 200 nm bundles comprise 50 nm clusters, cross-section SEM micrographs of the STF, and XPS spectra for flat and STF dicholoro [2.2] paracyclophane film.

FIG. 2 shows a cross-section scanning electron microscope (SEM, Philips XL-30) image, FIG. 2, panel (a) and a top-surface atomic force microscopy (AFM) image, FIG. 2, panel (b) of a STF (of parylene C) deposited for ten minutes on a silicon substrate, this type of substrate being compatible with scanning electron microscopy and infrared microscopy. Very clearly, FIG. 2 confirms that paracyclophane STF are assemblies of shaped nanowires. Furthermore, the AFM image of FIG. 2, panel (a), shows that the 200 nm clusters are made of 50 nm diameter columns. X-ray Photoelectron Spectra (XPS, Kratos Analytical Axis Ultra Brand) of the STF and flat samples are shown in panel (d) of FIG. 2. The XPS analysis of both samples produces very similar spectra for the carbon (285 eV) and chlorine peaks (272 and 201 eV). Together with the AFM results, we can conclude that the surface chemistry of the STF film is same as the flat film but the morphology is different (i.e. nanostructured based on SEM and AFM pictures).

Clarification of the definition of "flat films" and "nanostructured polymer STFs" is needed, at this stage. The "flat film" is the conventionally deposited paracyclophane film and it does not have any morphology or structure. The "STF" is the nanostructured paracyclophane film deposited using the described methodology.

The type-C parylene is the polymer form of the low-molecular-weight dimer of para-chloro-xylylene. The parylene starts with a dimer, which is placed in a vacuum system and converted to a reactive vapor of monomer by pyrolyzing for polymer formation. The chemical formula of the parylene-C monomer is $C_8H_7Cl$. The amount of this dimer was the only adjustable deposition parameter. Depositions were made in a commercial parylene reactor that had been modified to combine chemical and physical vapor deposition processes specifically for direct one-step fabrication of polymeric STFs. The deposition rate and the deposition pressure were controlled by the evaporation temperature (155° C.) of the dimer and the pyrolyzing temperature (690° C.). 0.7 g of parylene-C dimer was inserted into the vaporizer for each deposition, during which process the vapor pressure was maintained at approximately 10 Torr. The thickness for all chiral STFs deposited was found to vary between 15 and 30 μm. Uniformity of STF pieces within an individual batch and between identical batches (e.g., for deposition onto different substrates) was qualitatively assessed by scanning electron microscopy.

Thus, a methodology for forming STFs, including STFs formed of polymers such as para-xylylene derivatives has been explained. This methodology may be used to form STFs which are biocompatible and bioactive for biological uses.

II. Biological use of Polymeric STFs

Nanoengineered materials may serve as simulative tools for studying the interactions, transport, and synthesis of biomolecules in confined environments. By mimicking successful elements of natural nanoscale architectures, we can create polymers that possess the surface properties of cells. Engineered surfaces have been used to control cell adhesion [7-10]. It is known that the topography of the surface alters proliferation, [11-13] and differentiation [14-16]. It has been also shown that submicron-scale features activate macrophage cell adhesion and regulate the amount of F-actin in cells [17]. However, the majority of the surfaces studied to date use micron-scale topographies. Recent research by Karuri et al has shown that cell attachment on silicon columnar films can be dependent on nanoscale topography [18]: nanostructured surfaces affect cell morphology of human corneal epithelial cells. However, the long-term degradation of silicon interacting with biofluids is problematic.

The nanostructured materials discussed above are sculptured thin films (STFs), which are assemblies of upright, parallel, shaped nanowires (or submicronwires) generally grown by vapor deposition techniques. STFs are deposited on a substrate from a directional vapor source, with the substrate orientation relative to vapor source dynamically manipulated during deposition. The morphology of STFs comprises clusters of 1-3 nm that coalesce into columns 50-300 nm diameter depending on the deposition material. Blending of nanoscale and microscale morphologies is also possible [20]. STFs can have densities as low as 20-30% of the bulk material. Being porous, STFs can be infiltrated with gases, liquids, liquid crystals, organic monomers and these infiltrating media can alter the host STF's biocompatible properties [20].

The present inventors have recognized the use of bioactive STFs for use in biomedical applications. The three major advantages of STFs for biomedical application are as follows: (i) The surface-to-volume ratio is very high in STFs and the available surface area increases by over two orders of magnitude in relation to the bulk material. (ii) The porosity of the films is controllable. Therefore, it is possible to engineer not only the surface properties of STFs but also 3-dimensional scaffolds. (iii) STFs can be made out of virtually any material and can be endowed with transverse architectures to provide the best possible substrate and coating material for biological attachment at the nanoscale.

Direct one-step fabrication of chiral STFs of parylene-C that have 100-300 nm size columnar features was explained above [21]. The morphology of the parylene-C STFs and para-xylylene derivatives make them excellent candidates for substrates to attach and grow human kidney cells. The deposition process is robust, cheap and does not require any lithography technique.

A. Human Kidney Cell Growth

Standard protocols were used to grow the HEK-293 cells, an adenovirus-transformed human kidney cell line (ATCC 1573 CRL), at 37° C. in a 5% $CO_2$ atmosphere, using multiwell plates depending on the number of films. Dulbecco's Modified Eagle Medium (DMEM) (supplemented with 10% fetal calf serum without antibiotics) was used as the growth media [24].

B. Protein Assay

We performed a protein assay using the Micro BCA Protein Assay kit from Pierce. Protein assays provide another control for cell growth. Four chiral STFs were prepared, of which one was seeded at 1:1 density, the second was seeded at 1:2 density, and two were unseeded to act as control films. One control film was incubated along with the two seeded films, but the other control film was not incubated in the media. The seeded samples were prepared according to the Pierce Micro BCA manual. The samples were initially washed twice with 0.9% saline solution, and then with 0.1% SDS+0.1N NaOH solution (warmed to 37° C.) was added to lyse the cells and solubilize proteins. The lysates were then pipetted to microtubes where they were diluted with the SDS+NaOH buffer 10X, 20X, and 50X.

C. Cell Imaging and Fixation (i) Scanning electron microscopy: The STF as well as bulk parylene samples were prepared using standard fixation protocols. Briefly, the cells were incubated in 2.0% glutaraldehyde in 0.1M cacodylate buffer (pH 7.4) at room temperature for 1 hour. This step was followed by secondary fixation (sample incubated in 1% osmium tetraoxide in 0.1M cacodylate buffer at room temperature for 1 hour) and serial dehydration. Samples were dehydrated and sputter-coated with gold-palladium.

(ii) Confocal: We used the Olympus Fluoview 300 confocal laser scanning microscope with two single-line lasers (Blue argon, 488 nm, and Red HeNe, 633 nm). Two different objectives were used for imaging (PlanApo 60X and UplanFL 40X). Localization of F-actin was determined by AlexaFluor 488-conjugated phalloidin staining. Briefly, at various time points after seeding, films were fixed in 10% formalin, extracted with PBS+0.15% Triton X-100, and stained with AlexaFluor 488 labeled phalloidin (Molecular Probes) diluted in PBS+1.5% BSA. Cell nuclei were localized by counterstaining with DRAQ5 (Biostatus, UK) diluted 1:500 in PBS.

D. Results

The key advantages of using a nanostructured surface for cell attachment are the increased specific surface area, porosity, and higher efficiency of conjugation due to nanostructure. In order to assess the adequacy of the deposited parylene-C STFs for the growth of human kidney cells, an array of microscopic techniques was employed. Scanning electron microscopy was first used to study the attachment and characterization of parylene surface together with the kidney cells. A confocal laser microscope and image processing were then used in conjunction with fluorescent probes.

FIG. 2 shows a cross-section SEM micrograph and a top-surface AFM image of a parylene-C chiral STF deposited for ten minutes on a silicon substrate, this type of substrate being compatible with scanning electron microscopy. Very clearly, FIG. 2 confirms that parylene-C STFs are assemblies of shaped nanowires that provide enhanced surface-to-volume ratios required of biocompatible substrates. Furthermore, the AFM image of FIG. 2, panel (b) shows that the 200 nm diameter columns are made of 50 nm clusters.

Figure 3A:
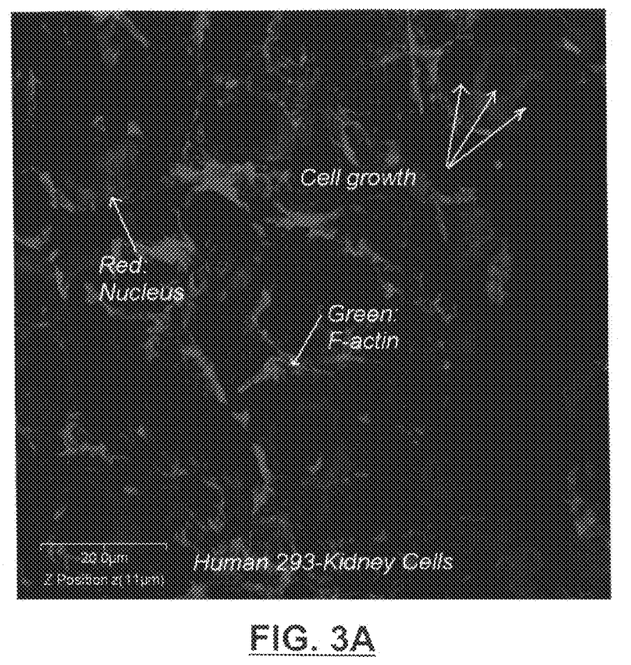
FIG. 3A and FIG. 3B are confocal laser microscope images exemplifying two-dimensional biofilm formation on chiral STFs.
Figure 3B:
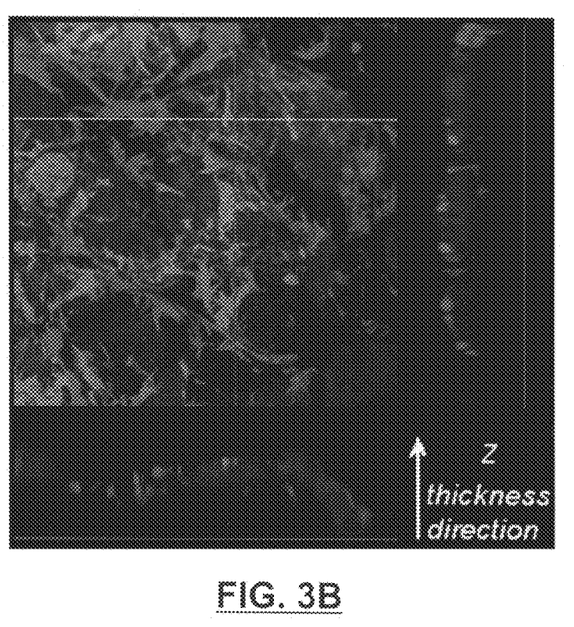

Human kidney 293 cells were grown on parylene-C STFs and bulk parylene-C films (control films). The cells were labeled with AlexaFluor 488-conjugated phalloidins and DRAQ5 dyes. Two-dimensional biofilm formation on chiral STFs was observed, as exemplified by the confocal laser microscope images in FIG. 3A and 3B, which show the fluorescent localization of F-actin and nucleic DNA. FIG. 3A and FIG. 3B unambiguously demonstrates the cell growth on and, thus, the biocompatibility of our STFs. Analysis of a series of confocal planes revealed that nuclei were localized near the outer cell surface distal to the growth surface. FIG. 3A shows a plane near the outer cell surface, 24 hours after seeding onto the STFs at 1:2 cell density. Several fields showed nuclei (red) undergoing division, thereby indicating continuing cell growth. Cross sections in FIG. 3B (side panels) demonstrate that cells formed monolayers on the films. Cells remained attached well to the chiral STFs throughout the numerous washing and staining steps. Cells adhered sufficiently well to neighbors that they could be released from the chiral STFs as single sheets after culturing under conditions which led to acidification and exhaustion of nutrients in the growth media.

Figure 4:
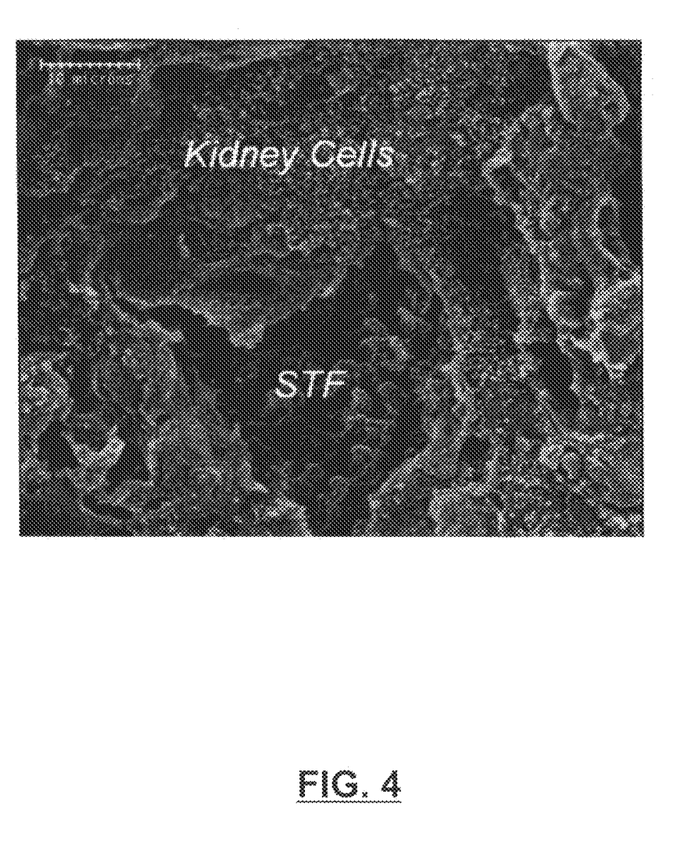
FIG. 4 is an image showing the topography and morphology of the STF and confirming the attachment of cells.

The top-surface morphology and cell attachment of the present invention has also been studied using scamling electron microcopy, since STFs are invisible to confocal laser microscopy. The kidney cells were fixated and we sputter-coated the surface with a gold-palladium alloy. FIG. 4 shows the topography and morphology of the STF and confirms the attachment of cells.

Figure 5A:
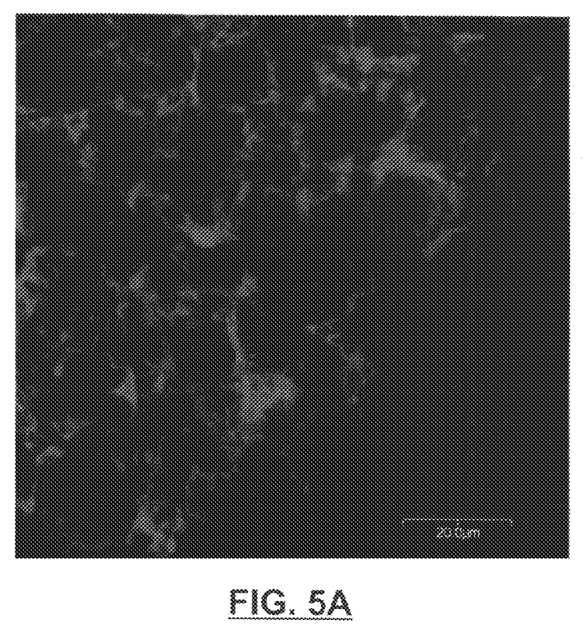
FIG. 5A and FIG. 5B are images showing the time course of differentiation of kidney cells on a parylene-C chiral STF.
Figure 5B:
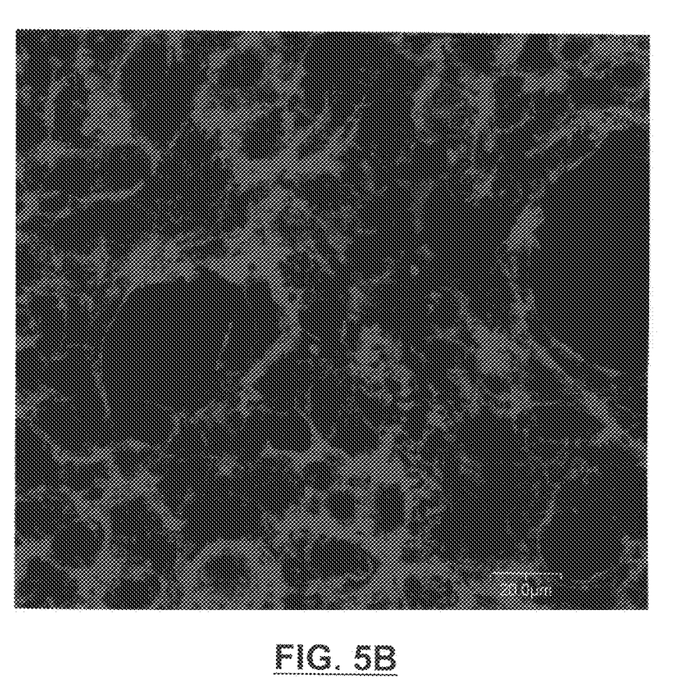
Figure 6:
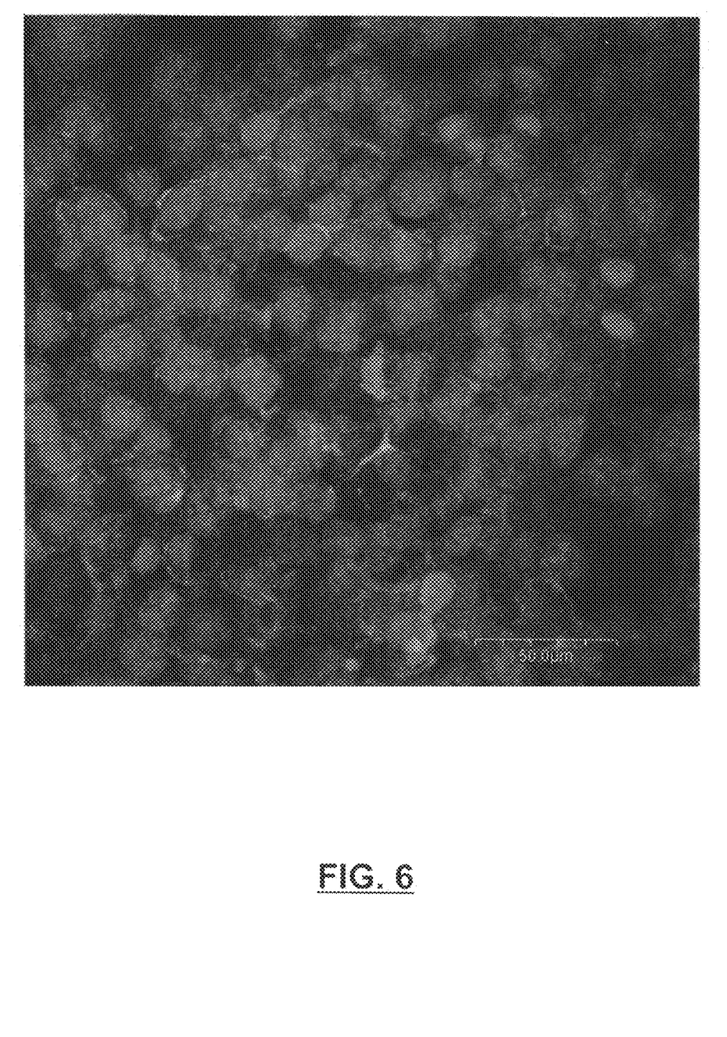
FIG. 6 is an image illustrating COS7 Fibroblast cells grown on nanoengineered STFs.

FIG. 5 shows the time course of differentiation of kidney cells on a parylene-C chiral STF. Films that have exact dimensions (5 mm square wafers) and same deposition conditions were prepared for this study. We examined the growth of fixated samples after 16, 24, and 36 hours using confocal laser microscopy. Control experiments with bulk (non-STF) parylene-C films incubated with culture media showed little or no cell growth. Cell growth on parylene-C chiral STFS after 16 hours was minimal (not shown); however, FIG. 5 demonstrates an increasing level of cell growth after 24 and 36 hours.

Kidney cells are on average 10 micron in size and form a two-dimensional biofilm on parylene-C STFs (FIG. 2). The production of STFs on 10 cm×10 cm substrates (industrial scale) appears possible with current technology [24]. As a result, it is possible to grow $5 \times 10^9$ kidney cells per STF film, assuming a conservative 50% growth efficiency.

The present inventors have provided herein a cheap and robust way of depositing polymeric sculptured thin films that have 100-300 nm size features. Nanoscale topography, especially compared to flat surfaces of bulk films, affects the cell adhesion of kidney cells and eventually dictates the cell fate on the substrate. The surface topography and porosity (that includes the third dimension perpendicular to the surface) of the STFs can be nanoengineered and controlled [20]. Also note that polymeric STF films are relatively cheap to deposit in comparison to e-beam lithography and other similar methods (i.e., just $0.5/(\mu m^* cm^2)$ including nanofabrication utility charges).

Nearly 900,000 patients worldwide suffering from kidney disease requires dialysis and about 21 percent of patients on dialysis on any year die [26]. Future studies on polymeric STFs may have two solutions to these patients suffering from kidney diseases: 1) the porous structure of a polymeric STF could be functionalized for dialysis, and 2) the parylene-C STFs, being highly bio-compatible in vivo, could be used as a coating material for artificial kidney devices.

The present invention contemplates that many different cell lines (including breast cancer cells, fibroblast cell lines) can be used with STF. The present invention further contemplates the use of probes for occludins and integrins to study the formation of tight junctions and the synthesis of attachment proteins, respectively. The present invention also contemplates the use of other polymers, including those well known for biocompatibility such as polyurethane and Teflon.

The present invention contemplates that the sculptured thin film can be used in numerous applications, including numerous medical applications. This includes, for example, use in medical devices, including intracorporeal as well as extracorporeal devices (e.g., catheters), temporary or permanent implants, stents, vascular grafts, anastomotic devices, aneurysm repair devices, embolic devices, and implantable devices (e.g., orthopedic implants).

The present invention contemplates use of sculptured thin films to prevent infections from opportunistic bacteria and other infectious micro-organisms, in some cases necessitating the removal of implantable devices. Such infections can also result in illness, long hospital stays, or even death. The present invention also contemplates prevention of infection on indwelling catheters, orthopedic implants, pacemakers, contact lenses, stents, vascular grafts, embolic devices, aneurysm repair devices and other medical devices.

The present invention contemplates use in accepting artificial implants by the surrounding tissues and by the body as a whole. In particular, the present invention contemplates the use of sculptured thin films to avoid irritating surround living structures, to avoid providing an abnormal inflammatory response, and to avoid inciting allergic or immunologic reactions.

The present invention further contemplates use with any number of devices or materials which interface with living systems, including fluids, such as fluids, cells, and tissues of the body as may be used in medicine and/or pharmaceutics.

Alternative drug-delivery systems that bring medication to targeted areas in the body also are widely sold. In one embodiment of the present invention, a drug delivery system is provides using sculptured thin films.

The present invention provides for nanoengineered sculptured thin films that are biocompatible and bioactive for the differentiation, proliferation and adhesion of eukaryotic and prokaryotic cellular matter, both in vitro and in vivo. Cell differentiation, proliferation and adhesion in vitro and in vivo are essential to successful research on and treatment of various diseases, disorders, and injuries to humans as well as animals. The complexity of the task has so far precluded success due to the incompatibility of substrate materials and architectures with cellular matter, because one or more of the differentiation, proliferation and adhesion processes degrade rapidly in time.

The present inventors have recognized and demonstrated the biocompatibility and bioactivity of nanoengineered sculptured thin films (STFs) of organic and inorganic materials (e.g., polymers, oxides and metals) that enable such biological applications. Certain medical applications would involve the coating of forming mandrels, catheters, guide wires, stents, sensors, transducers and probes with the bioactive STFs. Other applications include substrates for biological cultures, implanted biosensors and neural interfaces, and to prevent fibrous encapsulation and thus increase mutual adherence of different pairs of tissue types. The present invention also contemplates providing a simultaneous delivery agent for drugs, nutrients, and genes in a controlled manner. In addition, the present invention can be used to provide structural support to maintain tissue integrity.

Therefore methods and systems for forming and using STFs have been disclosed. It is to be understood that the present invention contemplates numerous variations within the spirit and scope of the claimed invention.

References

All references listed throughout the Specification, including the references listed below are herein incorporated by reference in their entireties.

(1) U.S. Pat. No. 5,866,204 to Robbie et al.
(2) U.S. Pat. No. 6,248,422 also to Robbie et al.
(3) A Lakhtakia, R Messier, M J Brett, K Robbie: Sculptured thin films (STFs) For Optical, Chemical, and Biological Applications. Innovations in Materials Research, Vol. 1, No. 2 (1996) 165-176.
(4) N Young, J Kowal: Optically Active Fluorite Films. Nature, Vol. 183 (1959) 104-105.
(5) E Dawon, N Young: Helical Kerr Cell. Journal of the Optical Society of America, Vol. 50(2) (1960) 170-171.
(6) T Motohiro, Y Taga: Thin film retardation plate by oblique deposition. Applied Optics, Vol. 28, No. 13 (1989) 2466-2482.
(7) S Buttiglieri, D Pasqui, M Migliori, H Johnstone, S Affrossman, L Sereni, M L Wratten, R Barbucci, C Tetta, G Camussi: Endothelization and adherence of leucocytes to nanostructured surfaces. Biomaterials 24 (2003) 2731-38.
(8) C D Wilkinson, M Riehle, M Wood, J Gallagher, A S G Curtis: The use of materials patterned on a nano- and micro-metric scale in cellular engineering. Materials Science & Engineering C-Biomimetic and Supraniiolecular Systems 19 (2002) 263-69.
(9) T J Webster, C Ergun, R H Doremus, R W Siegel, R Bizios: Enhanced functions of osteoblasts on nanophase ceramics. Biomaterials 21 (2000) 1803-10.
(10) J Q Liu, Q Zhang, E E Remsen, K L Wooley: Nanostructured materials designed for cell binding and transduction. Biomacromolecules 2 (2001) 362-68.
(11) J Folkman, A Moscona: Role of cell shape in growth control. Nature 273 (1978) 345-49.
(12) C S Chen, M Mrksich, S Huang, G M Whitesides, D E Ingber: Geometric control of cell life and death. Science 276 (1997) 1425-28.
(13) R Singhvi, A Kumar, G P Lopez, G N Stephanopoulos, D I C Wang, G M Whitesides, D E Ingber: Engineering Cell-Shape and Function. Science 264 (1994) 696-98.
(14) F M Watt, P W Jordan, C H Oneill: Cell-Shape Controls Terminal Differentiation of Human Epidermal-Keratinocytes. Proceedings of the National Academy of Sciences of the United States of America 85 (1988) 5576-80.
(15) J E Aubin, F Liu, L Malaval, A K Gupta: Osteoblast and Chondroblast Differentiation. Bone 17 (1995) S77-S83.
(16) S A Lelievre, V M Weaver, J A Nickerson, C A Larabell, A Bhaumik, O W Petersen, M J Bissell: Tissue phenotype depends on reciprocal interactions between the extracellular matrix and the structural organization of the nucleus. Proceedings of the National Academy of Sciences of the United States of America 95 (1998) 14711-16.
(17) B Wojciak-Stothard, A S G Curtis, W Monaghan, M McGrath, I Sommer, C D W Wilkinson: Role of the cytoskeleton in the reaction of fibroblasts to multiple grooved substrata. Cell Motility and the Cytoskeleton 31 (1995) 147-58.
(18) N W Karuri, S Liliensiek, A I Teixeira, G Abrams, S Campbell, P F Nealey, C J Murphy: Biological length scale topography enhances cell-substratum adhesion of human corneal epithelial cells. Journal of Cell Science 117 (2004) 3153-64.
(19) A Lakhtakia, W S Weiglhofer: On Light-Propagation in Helicoidal Bianisotropic Media. Proceedings of the Royal Society of London Series a-Mathematical and Physical Sciences 448 (1995) 419-437.
(20) A Lakhtakia, R Messier: Sculptured Thin Films: Nanonengineered Morphology and Optics, SPIE Press, Bellingham, Wash. 2005.
(21) S Pursel, M W Horn, M C Demirel, A Lakhtakia: Growth of sculptured polymer submicronwire assemblies by vapor deposition. Polymer 46 (2005) 9544-48.
(22) P Kramer, A K Sharma, H Yasuda: Polymerization of Para-Xylylene Derivatives (Parylene Polymerization) I. Deposition Kinetics for Parylene N and Parylene C. J. Polym. Sci., Polym. Chem., 22 (1984) 475-491.
(23) J A Hengst, J S Bond: Transport of meprin subunits through the secretory pathway—Role of the transmemberance and cytoplasmic domains and oligomerization. Jornal of Biological Chemistry 279 (2004) 34856-64.
(24) M W Horn, M D Pickett, R Messier, A Lakhtakia: Blending of nanoscal and microscale in uniform large-area sculptured thin-film architectures. Nanotechnology 15 (2004) 303-10.
(25) A R Nissenson, A J Collins, J Hurley, H Petersen, B J G Pereira, E P Steinberg: Opportunities for improving the care of patients with chronic renal insufficiency: Current practice patterns. Journal of the American Society of Nephrology 12 (2001) 1713-20.

What is claimed is:

1. A sculptured thin film biological system, comprising:
a sculptured thin film comprising a plurality of sculptured thin film para-xylylene derivative polymer nanowires having a diameter of about 50-300 nm;
a population of biological cells attached to the sculptured thin film;
wherein the sculptured thin film is biocompatible and bioactive relative to the cells and wherein the para-xylylene derivative polymer is of the formula:

where each of $R^1$, $R^2$, $R^3$, and $R^4$ is independently selected from H, COOH, $CH_2OH$, $CH_2OCH_3$, $COOCH_3$, $COCF_3$, and halogen.

2. The system of claim 1, further comprising:
a substrate connected to the sculptured thin film, wherein the substrate is adapted to deliver one or more compounds to the cells from the sculptured thin film.

3. The system of claim 2, wherein one or more of the compounds is a drug.

4. The system of claim 2, wherein one or more of the compounds is a nutrient that supports growth of the cells.

5. The system of claim 2, wherein one or more of the compounds is a gene.

6. The system of claim 2 wherein the sculptured thin film is functionalized with a biocompatible material.

7. The system of claim 2 wherein the population of cells is a biological tissue.

8. The system of claim 1 wherein the sculptured thin film has nucleation sites.

9. The system of claim 1 wherein the sculptured thin film further comprises biocompatible polymers that are not para-xylylene derivative polymers.

10. The system of claim 1 wherein each of $R^1$, $R^2$, $R^3$, and $R^4$ is selected from $CH_2OH$, $CH_2OCH_3$, $COOCH_3$, $COCF_3$, and halogen.

11. The system of claim 1, wherein each of $R^1$, $R^2$, $R^3$, and $R^4$ is selected from $COCF_3$, $COOCH_3$, and chloro.

12. The system of claim 1 wherein the wires are columnar columns.

13. The system of claim 1 wherein the wires are helical columns.

14. The system of claim 1 wherein the wires are distinct.

15. The system of claim 1 wherein the wires are interwoven.

16. The system of claim 1 wherein the wires are chevron shaped columns.

17. The system of claim 1 wherein the wires are chiral shaped columns.

18. The system of claim 1 further comprising a biomedical device having a substrate surface on which the sculptured thin film is deposited.

19. The system of claim 1 wherein the wires have a diameter of between about 100 nm and 300 nm.

20. The method system of claim 1 wherein the wires have a diameter of between about 100 nm and 200 nm.

21. The system of claim 1 wherein the sculptured thin film has a porosity sufficient to assist with the cell differentiation, proliferation, and adhesion.

22. The system of claim 1 further comprising an artificial device with a substrate surface adapted for use in a biological system, the substrate surface being at least partially covered by the sculptured thin film.

23. The system of claim 22 wherein the artificial device is an implantable medical device.

24. The system of claim 22 wherein the artificial device is a prosthetic device.

25. A method of forming a sculptured thin film on a surface, comprising:
rotating the surface; and
depositing a sculptured thin film comprised of a para-xylylene derivative polymer on the surface to form nanowires having a diameter of about 50-300 nm
wherein the para-xylylene derivative polymer is of the formula:

where each of $R^1$, $R^2$, $R^3$, and $R^4$ is independently selected from H, COOH, $CH_2OH$, $CH_2OCH_3$, $COOCH_3$, $COCF_3$, and halogen.

26. The method of claim 25 wherein the depositing step includes a physical vapor deposition and a chemical vapor deposition.

27. The method of claim 26 wherein the physical vapor deposition includes directional evaporation.

28. The method of claim 26 wherein the chemical vapor deposition includes pyrolysis of a paracyclophane compound of the formula:

where each of $R^1$, $R^2$, $R^3$, and $R^4$ is independently selected from H, COOH, $CH_2OH$, $CH_2OCH_3$, $COOCH_3$, $COCF_3$, and halogen.

29. The method of claim 25 wherein the depositing step comprises:
pyrolizing a paracyclophane compound into a vapor of monomers, wherein the paracyclophane compound is of the formula:

where each of $R^1$, $R^2$, $R^3$, and $R^4$ is independently selected from H, COOH, $CH_2OH$, $CH_2OCH_3$, $COOCH_3$, $COCF_3$, and halogen;
directing the vapor of monomers towards the surface while rotating the surface; and polymerizing the monomers on the surface.

30. A method of forming a sculptured thin film on a surface, comprising:
rotating the surface;
pyrolizing a paracyclophane compound into a vapor of monomers, wherein the paracyclophane compound is of the formula:

where each of $R^1$, $R^2$, $R^3$, and $R^4$ is independently selected from H, COOH, $CH_2OH$, $CH_2OCH_3$, $COOCH_3$, $COCF_3$, and halogen;
directing the vapor of monomers towards the surface while rotating the surface;
forming a plurality of sculptured thin film wires through polymerization of the monomers on the surface, each of the sculptured thin film wires having a diameter of between about 50 and 300 nm;
wherein the step of rotating the surface controls shape of the sculptured thin film wires and wherein the para-xylylene derivative polymer is of the formula:

where each of $R^1$, $R^2$, $R^3$, and $R^4$ is independently selected from H, COOH, $CH_2OH$, $CH_2OCH_3$, $COOCH_3$, $COCF_3$, and halogen.

31. The method of claim 30 wherein the polymer is biocompatible and bioactive.

32. The method of claim 25 wherein a morphology of the thin film is modified by changing a rotational parameter of the surface selected from one or more of speed, tilt, rock, and twist.

33. A method of using the sculptured thin film system of claim 1,
wherein the use is biological.

34. The method of claim 33 wherein the biological use comprises differentiation, proliferation and adhesion of eukaryotic and prokaryotic cellular matter.

* * * * *